(12) United States Patent
Tang

(10) Patent No.: US 8,471,208 B1
(45) Date of Patent: Jun. 25, 2013

(54) NON-DISPERSIVE INFRARED (NDIR) GAS SENSOR

(76) Inventor: Patrick Tang, Fremont, CA (US)

( * ) Notice: Subject to any disclaimer, the term of this patent is extended or adjusted under 35 U.S.C. 154(b) by 70 days.

(21) Appl. No.: 13/039,187

(22) Filed: Mar. 2, 2011

(51) Int. Cl.
*G01J 5/02* (2006.01)
(52) U.S. Cl.
USPC ........................................ 250/343; 250/341.1
(58) Field of Classification Search
USPC .............................................. 250/341.1, 343
See application file for complete search history.

(56) References Cited

U.S. PATENT DOCUMENTS

| | | | |
|---|---|---|---|
| 3,973,848 A * | 8/1976 | Jowett et al. | 356/51 |
| 5,819,756 A | 10/1998 | Mielordt | |
| 6,491,881 B2 | 12/2002 | Fryer et al. | |
| 7,214,939 B1 | 5/2007 | Wong | |
| 2005/0154539 A1 * | 7/2005 | Butler et al. | 702/22 |
| 2008/0035848 A1 | 2/2008 | Wong | |

* cited by examiner

*Primary Examiner* — Marcus Taningco
(74) *Attorney, Agent, or Firm* — Edward B. Weller

(57) ABSTRACT

A non-dispersive infrared gas sensor provides the same light path for light used in a reference mode and a test mode for testing for the presence or concentration of one or more gases. A vacuum is formed in the light pipe in the reference mode. Gas flows into the light pipe before the test mode. The same emitter and detector maybe used for both the test and reference modes. The emitter transmits an electromagnetic wave through the light pipe in both the reference and test modes. The detected signals in both modes are compared to determine the concentration or presence of gas in the light pipe.

20 Claims, 5 Drawing Sheets

NON-DISPERSIVE INFRARED (NDIR) GAS SENSOR

FIELD

The present invention relates to a gas sensor, and more particularly to a non-dispersive infrared gas sensor.

BACKGROUND

Many greenhouse gases absorb infrared radiation in a 4-12 µm wavelength region, as shown in FIG. 1, which is a graph of the absorption of infrared radiation by $CO_2$ gas as a function of wavelength. Present non-dispersive sensors rely upon an infrared (IR) source like a filament bulb or an LED/laser together with filters and a light pipe to carry out the analysis. Present non-dispersive sensors use one of two approaches for determining the concentration of gas analyzed.

FIG. 2 is a diagram illustrating a conventional gas sensor system 200 using a first approach in which the system 200 determines a ratio of a test system 202 against a reference system 212. The test system 202 comprises a light pipe 203, an emitter 204. and a detector 206. The light pipe 203 is open at both ends to allow a gas under test to flow through the light pipe 203. The emitter 204 and the detector 206 are disposed at opposite ends of the light pipe 203 so that light emitted by the emitter 204 propagates through the gas in the light pipe 203 and is partially absorbed if the light emitted by the emitter 204 is at an absorption frequency of the gas that is being tested for. The reference system 212 comprises a light pipe 213, an emitter 214, and a detector 216. The light pipe 213 is sealed and typically contains a vacuum or an inert gas. The emitter 214 and the detector 216 are disposed at opposite ends of the light pipe 213. The conventional gas sensor system 200 detects the received signals at the detectors 206 and 216, and compares the test signal in the test system 202 to a reference beam in the reference system 212 that is at a non-absorbing infrared wavelength.

The conventional gas sensor system 200 requires duplication of hardware (e.g., two emitters, two detectors, and two light pipes), and an optical sensing path in the light pipe 203 that must be keep clean.

FIG. 3 is a diagram illustrating a conventional gas sensor system 300 using a second approach in which the system 300 determines a ratio of two infrared signals in a common path. The conventional gas sensor system 300 comprises a first emitter 304 that generates an infrared beam having a first frequency that is directed towards a mirror 303 and a first detector 306 for detecting an infrared beam having the first frequency that is reflected from the mirror 303. The conventional gas sensor system 300 comprises a second emitter 314 that generates an infrared beam having a second frequency that is directed towards the mirror 303 and a second detector 316 for detecting an infrared beam having the second frequency that is reflected from the mirror 303.

The conventional gas sensor system 300 detects the received signals at the detectors 306 and 316, and compares the two detected signals to each other. By selecting the second frequency to be at a frequency that the gas under test does not absorb, the ratio of the compared signals is indicative of whether the gas under test is the gas that is being tested for.

The conventional gas sensor system 300 is prone to error because of unknown contaminants in the light path that have unknown frequency absorption characteristics. Further, a second emitter and a second detector are required.

What is needed is a system and method for detecting gases with less hardware and less errors due to contamination.

SUMMARY

A non-dispersive infrared gas sensor provides the same light path for light used in a reference mode and a test mode for testing for the presence or concentration of one or more gases. The same emitter and detector may be used for both the test and reference modes.

In one aspect, a non-dispersive infrared gas sensor comprises a substrate, an emitter, a detector, and a light pipe. The emitter and the detector are disposed on the substrate. The emitter and the detector are disposed adjacent to first and second openings, respectively, of the light pipe. The emitter is configured to provide an electromagnetic wave through the first opening of the light pipe in response to a first control signal. The detector is configured to generate an output signal in response to a received electromagnetic wave from the second opening of the light pipe. The light pipe has an inner surface to reflect the electromagnetic waves so that the electromagnetic waves propagate from the first opening to the second opening. A gas flow system extracts gas from the light pipe and allows gas to flow into the light pipe.

The non-dispersive infrared gas sensor further comprises a controller that is configured to control the gas flow system to extract gas from the light pipe in a first operational mode and to control the gas flow system to flow gas into the light pipe in a second operational mode. The controller is further configured to provide the first control signal to the emitter and to receive the output signal from the detector in the first operational mode, and to provide the first control signal to the emitter and to receive the output signal from the detector in the second operational mode. The controller is also configured to calculate a ratio of the output signal from the detector in the second operational mode and the output signal from the detector in the first operational mode.

In other aspects, the controller is further configured to determine a concentration of the gas present in the light pipe in the second operational mode based on the ratio.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF THE DRAWINGS

FIG. 4b is a front exploded perspective view of the non-dispersive Infrared (NDIR) gas sensor of FIG. 4a.

FIG. 4c is a front partially cutaway perspective view of the non-dispersive Infrared (NDIR) gas sensor of FIG. 4a.

FIG. 5a is a back perspective view of the non-dispersive Infrared (NDIR) gas sensor of FIG. 4a.

FIG. 5b is a back exploded perspective view of the non-dispersive Infrared (NDIR) gas sensor of FIG. 4a.

FIG. 5c is a back partially cutaway perspective view of the non-dispersive Infrared (NDIR) gas sensor of FIG. 4a.

FIG. 6 is a block diagram illustrating a control system of the non-dispersive Infrared (NDIR) gas sensor of FIG. 4a.

DETAILED DESCRIPTION

Various embodiments are now described with reference to the figures where like reference numbers indicate identical or functionally similar elements. Also in the figures, the left most digits of each reference number corresponds to the figure in which the reference number is first used.

Reference in the specification to "one embodiment", "an embodiment", "various embodiments" or "some embodiments" means that a particular feature, structure, or characteristic described in connection with these embodiments is included in at least one embodiment of the invention, and such references in various places in the specification are not necessarily all referring to the same embodiment.

A non-dispersive Infrared (NDIR) gas sensor comprises an emitter and a detector formed on a single substrate and disposed adjacent to a corresponding opening in a light pipe that communicates electromagnetic waves from the emitter to the detector through a vacuum or a gas within the light pipe. Light from the emitter is passed through the light pipe in two states of the light pipe, such as when the light pipe has a vacuum therein and when a gas is present. The common path for the two states allows for contamination of the light pipe because the contamination is common for the two states. The detected light in the two states is compared and a gas concentration and a gas presence can be determined.

By fabricating the emitter and detector from the same semiconductor chip provides a smaller die-size and cost saving. Further, forming the emitter and detector next to each other on the same chip provides auto-temperature compensation.

Forming the emitter and detector in the same region of the same wafer provides increased yield in manufacturing. The emitter and detector are heterostructures, and thus are therefore matched for light emission and detection.

The NDIR gas sensor may be formed without a reference cell or a second emitter/detector for measuring a reference signal.

Figure 1:
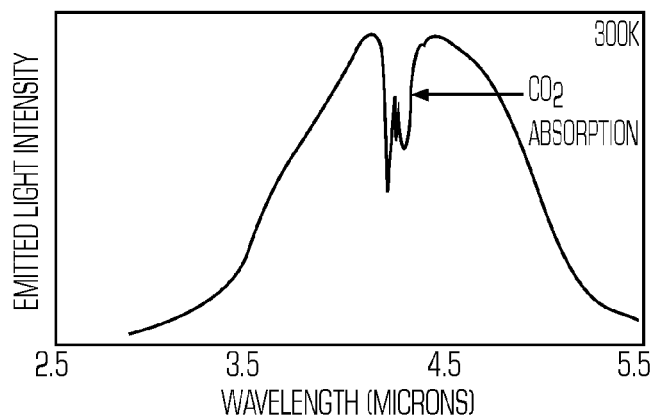
FIG. 1 is a graph of the absorption of infrared by $CO_2$ gas as a function of frequency.
Figure 2:
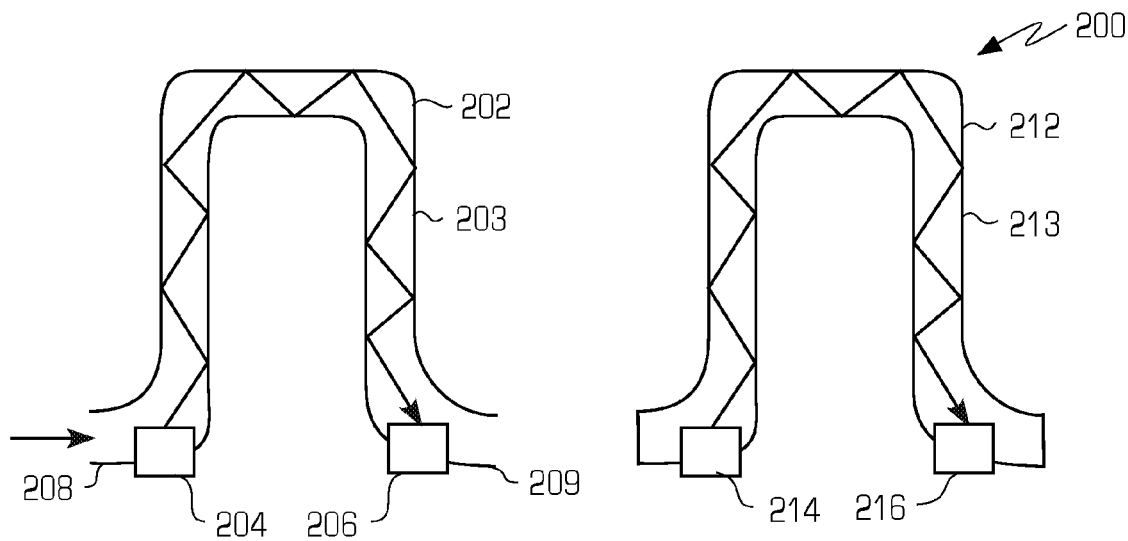
FIG. 2 is a diagram of a conventional sensor system using a reference path that is separate from a test path.
Figure 3:
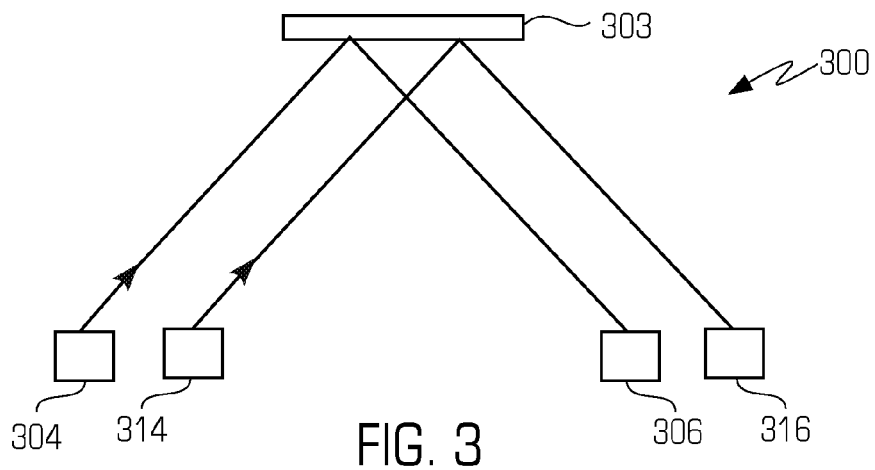
FIG. 3 is a diagram of a conventional sensor system using two different frequency signals in a common path.
Figure 4A:
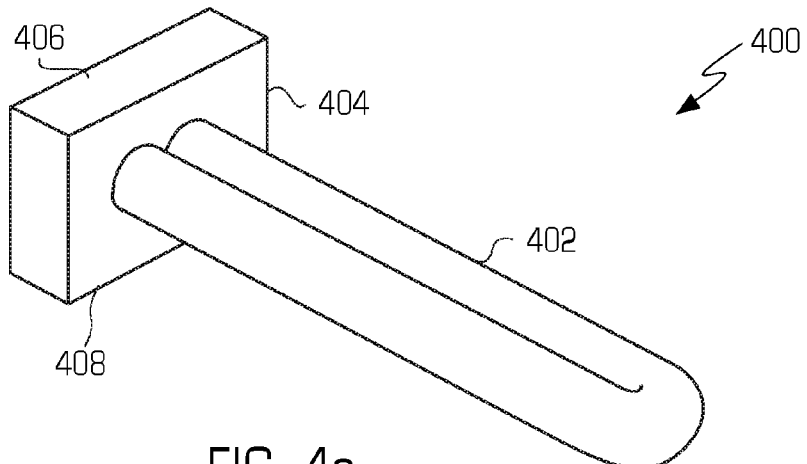
FIG. 4a is a front perspective view of a non-dispersive Infrared (NDIR) gas sensor.
Figure 4B:
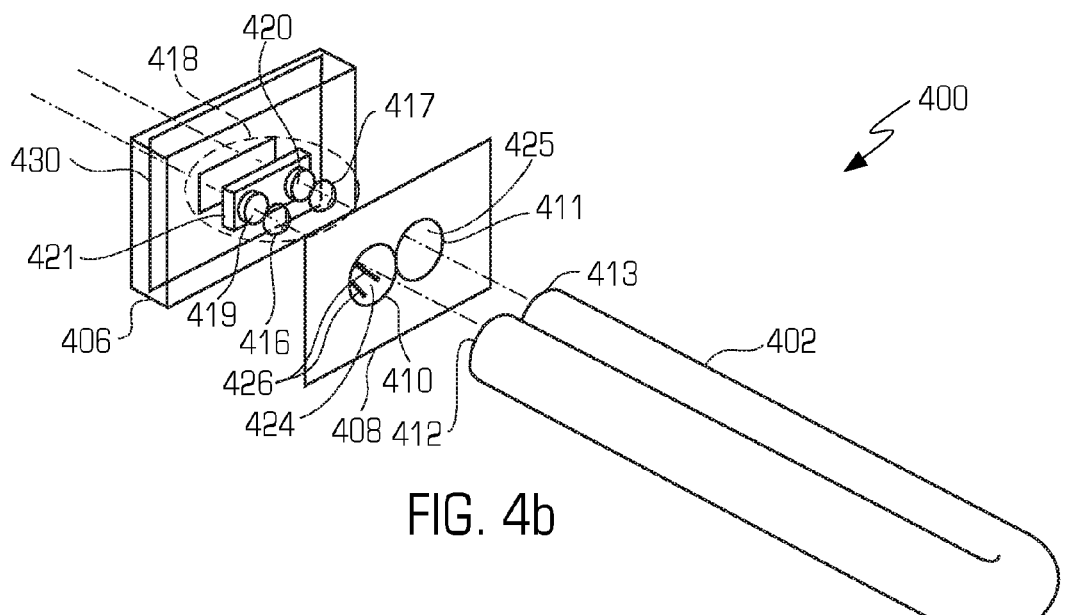
Figure 4C:
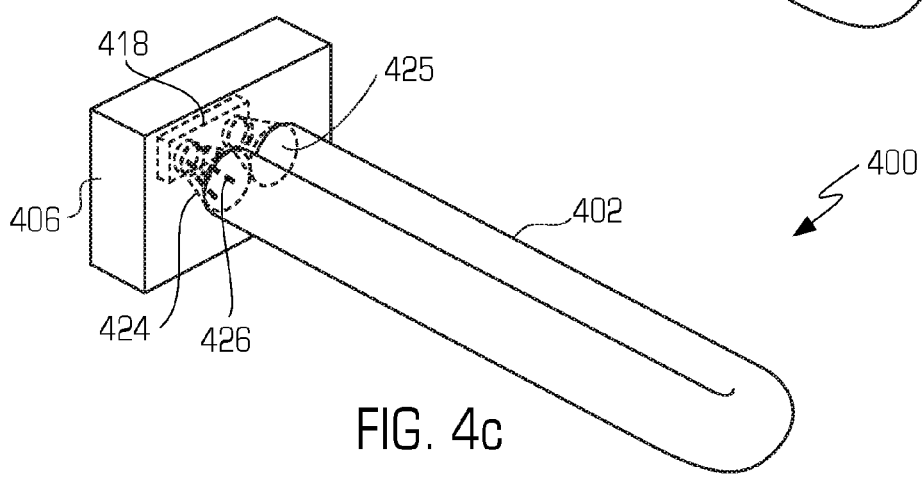

FIG. 4a is a front perspective view of a non-dispersive Infrared (NDIR) gas sensor 400. FIG. 4b is a front exploded perspective view of the non-dispersive Infrared (NDIR) gas sensor 400. FIG. 4c is a front partially cutaway perspective view of the non-dispersive Infrared (NDIR) gas sensor 400.

The non-dispersive Infrared (NDIR) gas sensor 400 comprises a light pipe 402 and a sensor system 404, which includes a housing 406 with a front face 408. The front face 408 has a pair of apertures 410 and 411 that are mounted to corresponding openings 412 and 413 in the light pipe 402. Cones 424 and 425 are disposed between the openings 412 and 413, respectively, in the light pipe 402 and an infrared system 418. The infrared system 418 comprises an emitter 419 and a detector 420 disposed on a substrate 421. Encapsulation lenses 416 and 417 are disposed at the emitter 419 and the detector 420, respectively. The encapsulation lenses 416 and 417 prevent the cones 424 and 425, respectively, from physically contacting, and thereby protecting, the emitter 419 and the detector 420. The substrate 421 and the infrared system 418 may be mounted on and electrically coupled to a detection system 430, which may be mounted on a circuit board. The detection system 430 is described in more detail below in conjunction with FIG. 6.

The light pipe 402 provides the same light path for a reference mode with gas purged from the light pipe 402 and a test mode with gas present in the light pipe 402 for measuring the signal strength of light signals propagating through the light pipe 402.

In some embodiments, the light pipe 402 has a U-shaped or a substantially U-shaped longitudinal cross-section and a circular or substantially circular transverse cross section. The light pipe 402 may have other cross-sectional shapes that allow light to propagate through the light pipe 402.

The light pipe 402 provides an electromagnetic path between the emitter 419 and the detector 420. The light pipe 402 has an inner surface that is reflective of the electromagnetic waves or infrared radiation emitted by the emitter 419. In some embodiments, the light pipe 402 is formed of aluminum and has an inner surface that is polished. In some embodiments, the infrared radiation undergoes multiple reflections back and forth in the light pipe 402 to thereby lengthen the electromagnetic path, and increase the infrared absorption by the gas in the light pipe 402.

The light cone 424 reflects light from the emitter 419 into the light pipe 402, and may include perforations 426 to allow the gas that is being analyzed to flow in and out of the light pipe 402. The light cone 425 concentrates the light on the detector 420. In some embodiments, the light cone 425 may include perforations.

The emitter 419 is configured to provide an electromagnetic wave having a fixed frequency, or alternatively variable selectable frequencies, in response to a control signal from the detection system 430. The emitter 419 is tuned to the infrared absorption band of the gas being test for. In some embodiments, the emitter 419 and the detector 420 are formed of semiconductors and are fabricated on the same chip or the same substrate 421 by photolithography and fabrication using standard processes. In various embodiments, the emitter 419 and the detector 420 are formed spaced apart and near or adjacent to each other on a substrate. The emitter 419 may be for example, infrared emitter (heterostructure semiconductor laser, quantum cascade laser or LED).

The detector 420 is configured to generate an output signal in response to a received electromagnetic wave and provide the output signal to the detection system 430. The detector 420 may be, for example, formed of semiconductor, pyroelectric or resistive materials.

The detection system 430 controls a gas flow system 502 (see FIGS. 5a, 5b, and 5c) to extract gas from the light pipe 402 in a first operational mode (e.g., a reference mode) and controls the gas flow system 502 to flow gas into the light pipe 402 in a second operational mode (e.g., a test mode). In the first and second operational modes, the detection system 430 provides control signals to the emitter 419 to emit light, which may be variable in frequency. The detection system 430 calculates a ratio of the output signal from the detector 420 in the second operational mode and the output signal from the detector 420 in the first operational mode. The detection system 430 determines a concentration of the gas present and/or whether a particular gas is in the light pipe 402 in the second operational mode based on the ratio and generate a control signal to display the concentration.

Figure 5A:
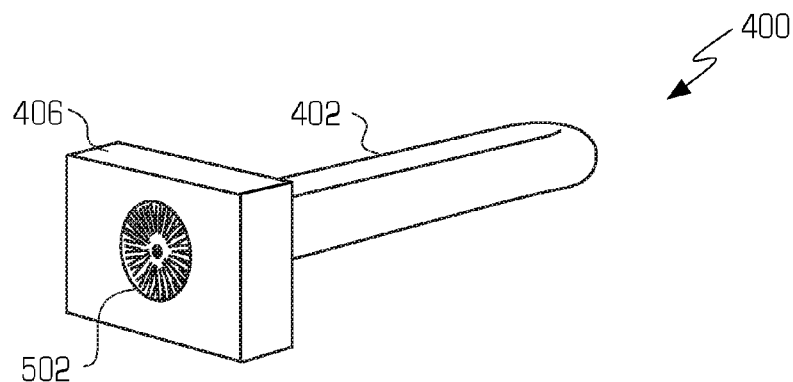
Figure 5B:
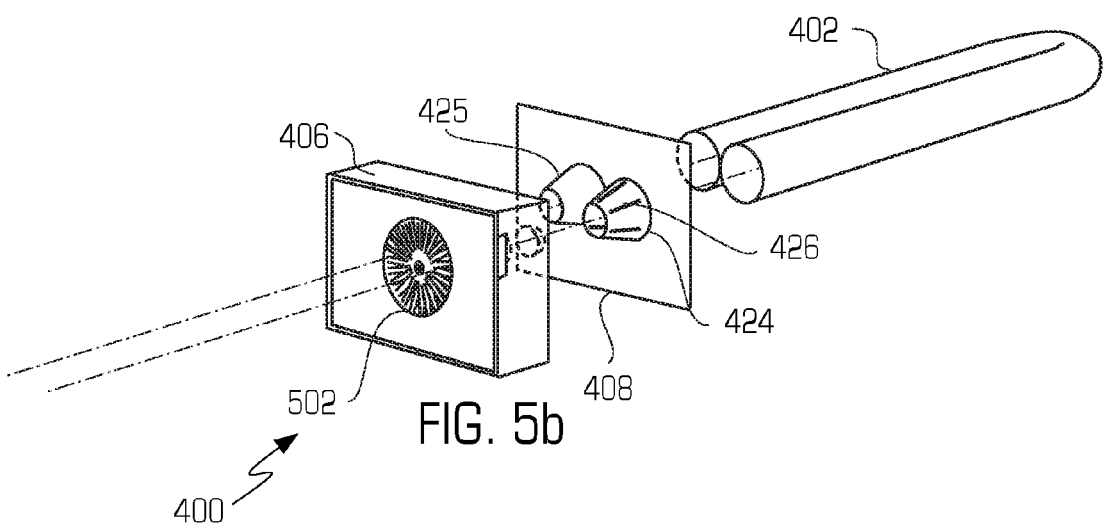
Figure 5C:
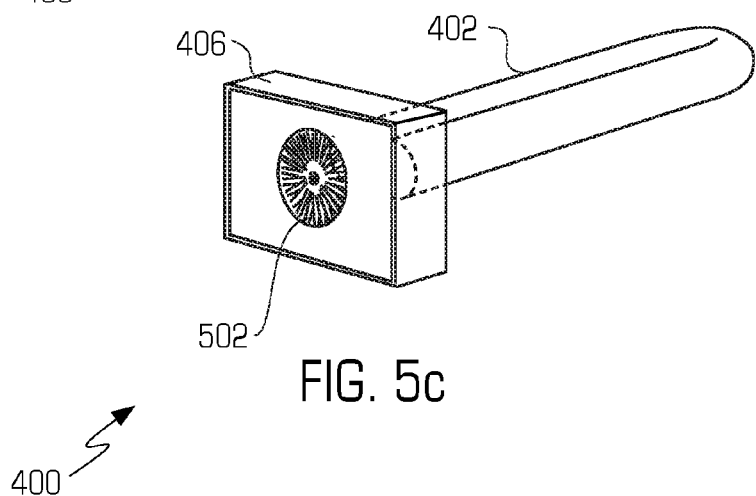

FIG. 5a is a back perspective view of the non-dispersive Infrared (NDIR) gas sensor 400. FIG. 5b is a back exploded perspective view of the non-dispersive Infrared (NDIR) gas sensor 400. FIG. 5c is a back partially cutaway perspective view of the non-dispersive Infrared (NDIR) gas sensor 400.

The NDIR gas sensor 400 further comprises a gas flow system 502 that extracts gas from the light pipe 402 and allows gas to flow into the light pipe 402. The gas flow system 502 may include, for example, a vacuum pump system or a fan. The housing 406 allows gas to flow out of the light pipe 402 through the housing 406 and drawn out of the housing 406 by the gas flow system 502. In some embodiments, the housing 406 includes gas flow channels between the gas flow system 502 and the cone 424. In some embodiments, the cone 424 may include a movable cover over the perforations 426 to selectively seal the light pipe 402 during the first operational mode after a vacuum is drawn in the light pipe 402 and to selectively open to allow more area for drawing a vacuum from the light pipe 402. In some embodiments, the light cone 425 may include perforations, and in various embodiments, the light cone 425 may include a movable cover over the perforations to selectively seal the light pipe 402 during the first operational mode after a vacuum is drawn in the light pipe 402 and to selectively open to allow more area for drawing a vacuum from the light pipe 402.

Figure 6:
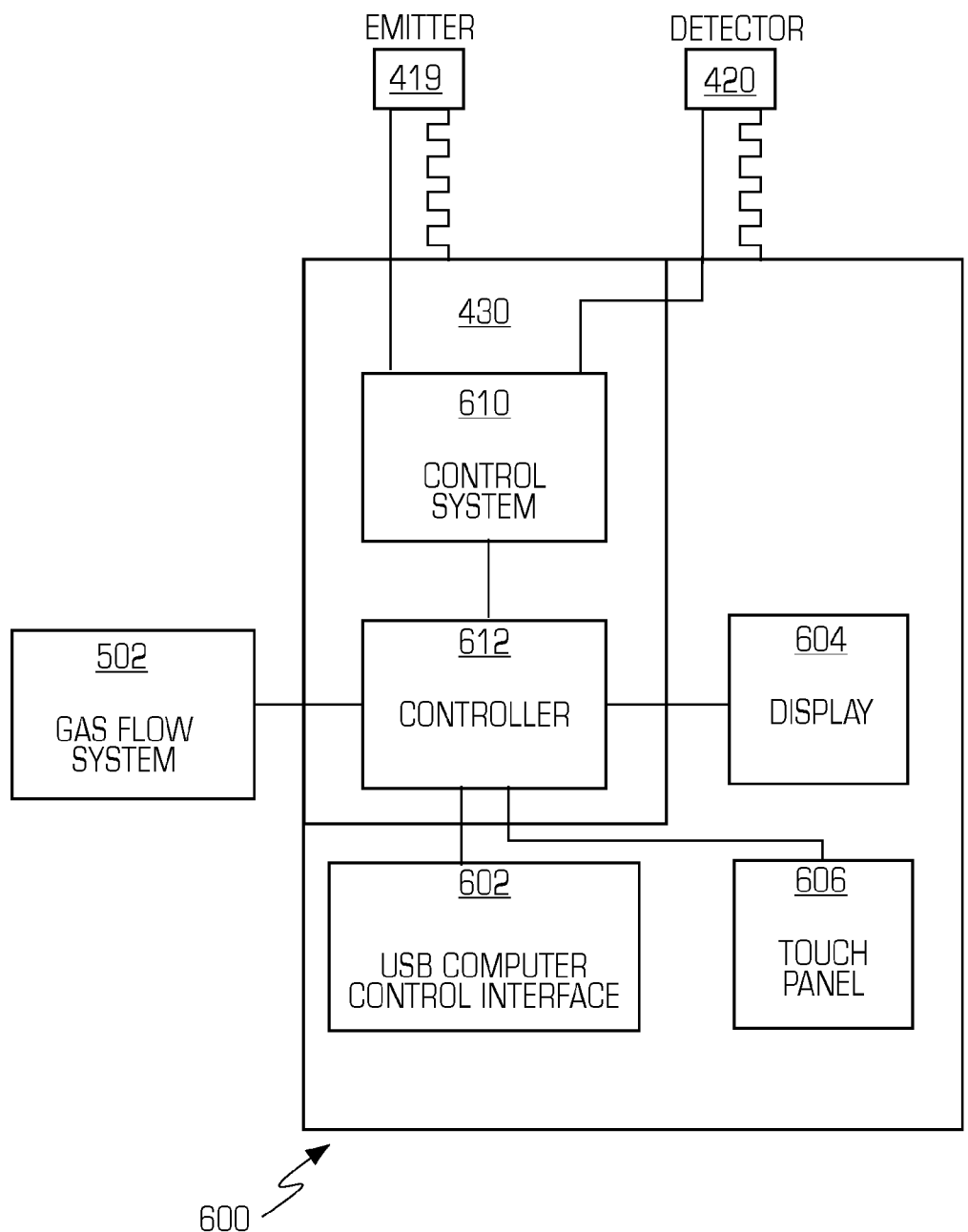

FIG. 6 is a block diagram illustrating a control system of the non-dispersive Infrared (NDIR) gas sensor 400.

The NDIR gas sensor 400 includes a gas sensing system 600 that comprises the detection system 430, an interface 602, a display 604 and a user interface 606. The interface 602 may be a universal serial bus (USB) computer interface that allows a user to have remote or direct control of the NDIR gas sensor 400. The display 604 may be any conventional display, such as a liquid crystal display. The user interface 606 provides local control of the NDIR gas sensor 400, and may be a touch pad, for example. The detection system 430 comprises a control system 610 and a controller 612.

The control system 610 provides control signals to the emitter 419, and receives and processes detected signals from the detector 420. The control system 610 may include an emitter pulse generator and a lock-in amplifier.

The controller 612 is coupled to the control system 610 to control the operation of the control system 610 and to receive data and control signals from the control system 610. The controller 612 is coupled to the gas flow system 502 for controlling the formation or removal of a vacuum in the light pipe 402. The controller 612 is coupled to the display 604 for providing information, such as gas concentration, gas type or gas absorption, to the user. The controller 612 is coupled to the interface 602 for communication with an external device (not shown), such as a computer, for external remote control by a user. The controller 612 is coupled to the user interface 606 for receiving user commands. The controller 612 may be an Application Specific Integrated Circuit (ASIC) or a processor. The controller 612 may include a memory for storing code and received and processed data.

Although particular partitioning of functions and operations between the control system 610 and the controller 612 are described, the invention is not so limited; other partitioning may be used.

Figure 7:
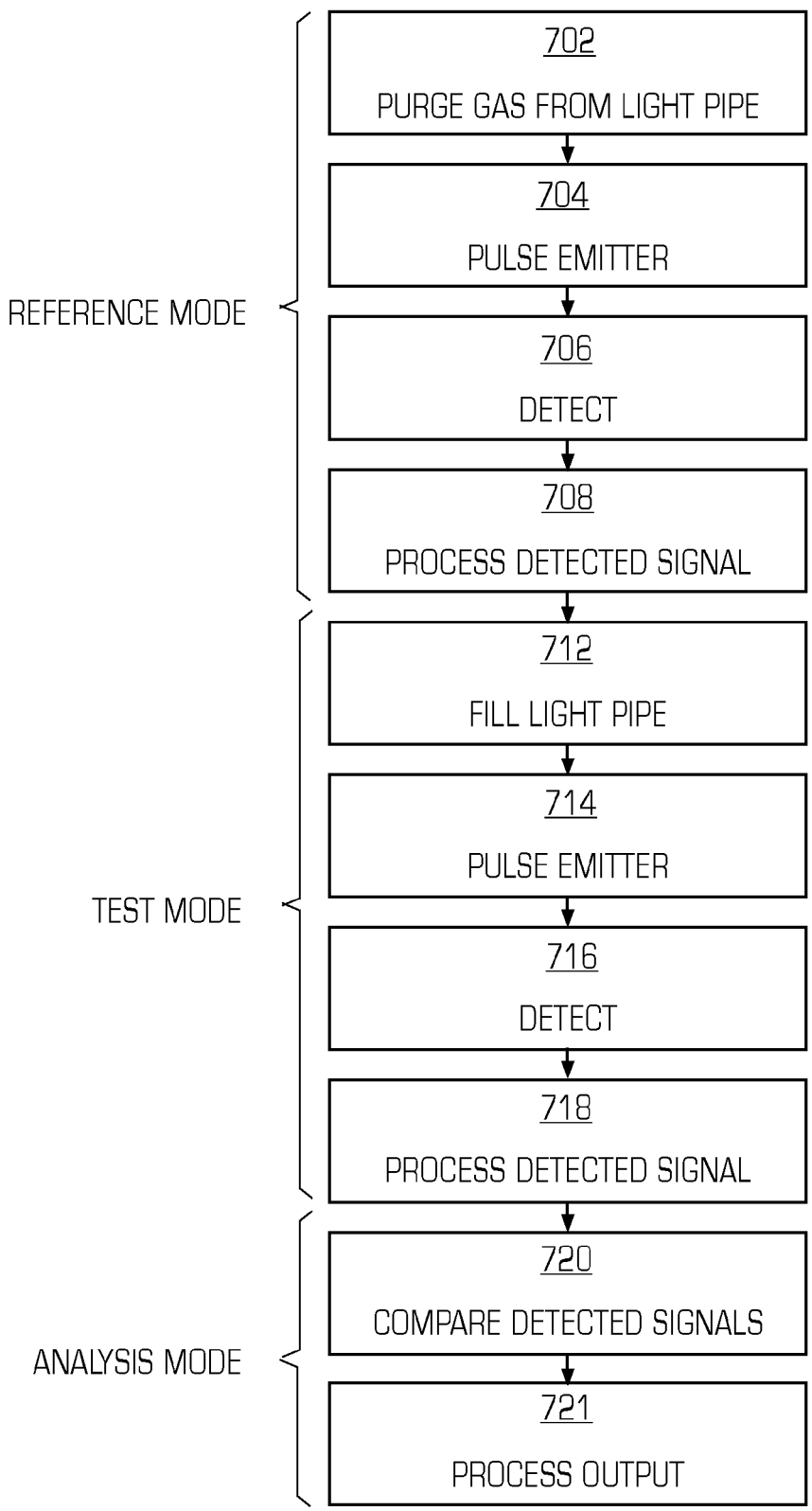
FIG. 7 is a flowchart illustrating the operation of the control system of FIG. 6.

FIG. 7 is a flowchart illustrating the operation of the NDIR gas sensor 400. In a reference mode, the controller 612 commands the gas flow system 502 to purge gas from the light pipe 402 (block 702). The controller 612 commands the control system 610 to pulse the emitter 419 (block 704). For a variable frequency emitter 419, the controller 612 commands the control system 610 to set the frequency of the emitter 419 to a frequency in the absorption band of the gas being tested for. The controller 612 commands the control system 610 to control the detector 420 to receive and detect the light passing through the light pipe 402 (block 706). The detection system 430 processes the detected signal (block 708). The controller 612 commands the control system 610 to lock in at the frequency of the current pulse frequency of the emitter 419, and amplify the signal detected by the detector 420. The control system 610 may integrate the detected signal over a predetermined or selected time (e.g., one second). The integration time can be varied to optimize between accuracy (longer integration time) and faster data acquisition (shorter integration time). The controller 612 records and stores the signal strength.

In a test mode, the controller 612 commands the gas flow system 502 to allow gas to flow into the light pipe 402 (block 712). The controller 612 commands the control system 610 to pulse the emitter 419 (block 714), and the detector 420 to receive and detect signals (block 716) in processes similar to the pulsing and detecting of blocks 704 and 706, respectively. The detection system 430 processes the detected signal (block 718) in similar manner as the processing of block 708. The processing during the test mode may be different from the processing in the reference mode. For example, the integration time may be longer to account for the weak absorption of the infrared due to low concentration of the gas species being detected.

The controller 612 compares the processed detect signals (of blocks 708 and 718) to determine the ratio of the detected signal under vacuum and the detect signal under gas and determines a concentration of the gas present.

To test for different gases, the controller 612 may repeat blocks 702-720 for different frequencies of infrared radiation from the emitter 419.

Some portions of the detailed description above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions described herein in the form of an algorithm. It should be noted that the process steps and instructions of the present invention could be embodied in software, firmware or hardware, and when embodied in software, could be downloaded to reside on and be operated from different platforms used by a variety of operating systems.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein, and any references below to specific languages are provided for disclosure of enablement and best mode of the present invention.

In addition, the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention, which is set forth in the claims.

What is claimed is:

1. A non-dispersive infrared gas sensor comprising:
    a substrate;
    an emitter disposed on the substrate and configured to provide an electromagnetic wave in response to a first control signal;
    a detector disposed on the substrate and configured to generate an output signal in response to a received electromagnetic wave;
    a light pipe having first and second openings, the first opening being disposed adjacent the emitter, the second opening being disposed adjacent the detector, the light pipe having an inner surface to reflect the electromagnetic waves so that the electromagnetic waves propagate from the first opening to the second opening;
    a gas flow system coupled to the light pipe to extract gas from the light pipe and to allow gas to flow into the light pipe; and
    a controller coupled to the emitter, the detector and the gas flow system, and configured to:
        control the gas flow system to extract gas from the light pipe to draw a vacuum in the light pipe in a first operational mode and to control the gas flow system to flow gas into the light pipe in a second operational mode,
        provide the first control signal to the emitter and to receive the output signal from the detector in the first operational mode while the vacuum is drawn in the light pipe,
        provide the first control signal to the emitter and to receive the output signal from the detector in the second operational mode, and
        calculate a ratio of the output signal from the detector in the second operational mode and the output signal from the detector in the first operational mode.

2. The sensor of claim 1, wherein the controller is further configured to determine a concentration of the gas present in the light pipe in the second operational mode based on the ratio and generate a control signal to display the concentration.

3. The sensor of claim 1, wherein the controller determines whether a particular gas is in the light pipe during the second operational mode based on the ratio.

4. The sensor of claim 1, wherein the emitter and the detector are disposed spaced apart on a surface of the substrate.

5. The sensor of claim 1 further comprising first and second encapsulant lenses disposed on the emitter and the detector, respectively.

6. The sensor of claim 1, wherein the emitter is disposed adjacent to the detector on a surface of the substrate.

7. The sensor of claim 1, wherein the light pipe has a U-shape.

8. The sensor of claim 1, wherein the light pipe has a substantially circular transverse cross-section.

9. The sensor of claim 1, wherein an inner surface of the light pipe is reflective of infrared radiation.

10. The sensor of claim 1, wherein the light pipe is formed of aluminum and, wherein an inner surface of the light pipe is polished.

11. The sensor of claim 1, wherein the light pipe includes perforations on the walls near the second opening.

12. The sensor of claim 1, wherein the light pipe includes a cone shaped region near the second opening.

13. The sensor of claim 1, wherein the emitter is configured to provide an electromagnetic wave having a frequency that is selectable in response to the first control signal.

14. The sensor of claim 13, wherein the frequency is in an absorbing band of a gas being tested for.

15. The sensor of claim 1, wherein the gas flow system comprises a fan.

16. The sensor of claim 1, wherein the gas flow system comprises a vacuum pump.

17. The sensor of claim 1, wherein the controller is further configured to process the output signal by integrating the output signal for a predetermined time.

18. A method for determining a presence of a gas, the method comprising:
    extracting gas from a light pipe in a first operational mode
    emitting an electromagnetic wave from an emitter disposed at a first end of the light pipe in the first operational mode;
    detecting a first output signal from a detector disposed at a second end of the light pipe in the first operational mode, the detector and the emitter being disposed on a substrate;
    allowing gas to flow into the light pipe in a second operational mode,
    emitting an electromagnetic wave from the emitter in the second operational mode;
    detecting a second output signal from the detector in the second operational mode;
    calculating a ratio of the first and second output signals.

19. The method of claim 18, further comprising determining a concentration of the gas present in the light pipe in the second operational mode based on the ratio.

20. The method of claim 18, further comprising determining whether a particular gas is in the light pipe during the second operational mode based on the ratio.

\* \* \* \* \*